United States Patent
Yu et al.

(10) Patent No.: US 11,416,986 B2
(45) Date of Patent: Aug. 16, 2022

(54) SIMULATING VISUAL FIELD TEST FROM STRUCTURAL SCANS

(71) Applicants: International Business Machines Corporation, Armonk, NY (US); New York University, New York, NY (US)

(72) Inventors: Hsin-Hao Yu, Mount Waverley (AU); Stefan Renard Maetschke, Ascot Vale (AU); Suman Sedai, Hughesdale (AU); Bhavna Josephine Antony, Brunswick East (AU); Rahil Garnavi, Macleod (AU); Hiroshi Ishikawa, Edgewater, NJ (US)

(73) Assignees: INTERNATIONAL BUSINESS MACHINES CORPORATION, Armonk, NY (US); NEW YORK UNIVERSITY, New York, NY (US)

( * ) Notice: Subject to any disclaimer, the term of this patent is extended or adjusted under 35 U.S.C. 154(b) by 373 days.

(21) Appl. No.: 16/846,661

(22) Filed: Apr. 13, 2020

(65) Prior Publication Data
US 2021/0319552 A1    Oct. 14, 2021

(51) Int. Cl.
*G06K 9/00*    (2022.01)
*G06T 7/00*    (2017.01)
(Continued)

(52) U.S. Cl.
CPC .......... *G06T 7/0012* (2013.01); *A61B 3/0025* (2013.01); *A61B 3/024* (2013.01);
(Continued)

(58) Field of Classification Search
CPC ......... G06T 7/0012; G06T 2207/10101; G06T 2207/30041; A61B 3/0025; A61B 3/024; A61B 3/102; A61B 3/145
See application file for complete search history.

(56) References Cited

U.S. PATENT DOCUMENTS 11,039,742 B1 *   6/2021  Abou Shousha ...... G06N 3/084
2017/0209044 A1 *   7/2017  Ito ........................... A61B 3/10
(Continued)

FOREIGN PATENT DOCUMENTS

CN           105011900 A       2/2018

OTHER PUBLICATIONS

Denniss, Jonathan, Andrew Turpin, and Allison M. McKendrick. "Relating optical coherence tomography to visual fields in glaucoma: structure—function mapping, limitations and future applications." Clinical and Experimental Optometry 102.3 (2019): 291-299. (Year: 2019).*

(Continued)

*Primary Examiner* — Avinash Yentrapati
(74) *Attorney, Agent, or Firm* — Cantor Colburn LLP; Joseph Petrokaitis

(57) ABSTRACT

Aspects of the invention include a computer implemented method for simulating visual field test results from structural scans, the method includes processing eye image data to extract visual functioning related features. Additionally, generating a representation of a visual function of the eye that is independent of a visual field test (VFT) configuration. Then generating a simulated VFT configuration specific test result based at least in part on the representation.

20 Claims, 6 Drawing Sheets

(51) Int. Cl.
*A61B 3/14* (2006.01)
*A61B 3/10* (2006.01)
*A61B 3/00* (2006.01)
*A61B 3/024* (2006.01)

(52) U.S. Cl.
CPC .............. *A61B 3/102* (2013.01); *A61B 3/145* (2013.01); *G06T 2207/10101* (2013.01); *G06T 2207/30041* (2013.01)

(56) References Cited

U.S. PATENT DOCUMENTS

| | | | |
|---|---|---|---|
| 2019/0269315 A1* | 9/2019 | Lu | A61B 3/0025 |
| 2020/0288971 A1* | 9/2020 | Huang | A61B 3/102 |
| 2021/0112226 A1* | 4/2021 | Abou Shousha | A61B 3/145 |

OTHER PUBLICATIONS

Denniss et al.,"Relating Optical Coherence Tomography to Visual Fields in Glaucoma: Structure—Function Mapping, Limitations and Future Applications", May 3, 2019. 9 Pages.

\* cited by examiner

SIMULATING VISUAL FIELD TEST FROM STRUCTURAL SCANS

BACKGROUND

The present invention generally relates to a computer-based modeling system, and more specifically, to simulating visual field test results from structural scans.

Slow-progressing eye diseases, such as glaucoma, requires long term monitoring of its progression. The current strategy for treating or managing the progression of these diseases requires both structural and functional assessments of the eye. A structural assessment is performed generally using imaging techniques, such as optical coherence tomography (OCT). A functional assessment is performed with visual field testing.

SUMMARY

Embodiments of the present invention are directed to the generation of a standard suite of visual function test results from eye imaging tests. A non-limiting example computer-implemented method for simulating visual field test results from structural scans includes processing eye image data to extract visual functioning related features. Additionally, generating a representation of a visual function of the eye that is independent of a visual field test (VFT) configuration. Then generating a simulated VFT configuration specific test result based at least in part on the representation.

Other embodiments of the present invention implement features of the above-described method in computer systems and computer program products.

Additional technical features and benefits are realized through the techniques of the present invention. Embodiments and aspects of the invention are described in detail herein and are considered a part of the claimed subject matter. For a better understanding, refer to the detailed description and to the drawings.

BRIEF DESCRIPTION OF THE DRAWINGS

The specifics of the exclusive rights described herein are particularly pointed out and distinctly claimed in the claims at the conclusion of the specification. The foregoing and other features and advantages of the embodiments of the invention are apparent from the following detailed description taken in conjunction with the accompanying drawings in which:

Figure 1:
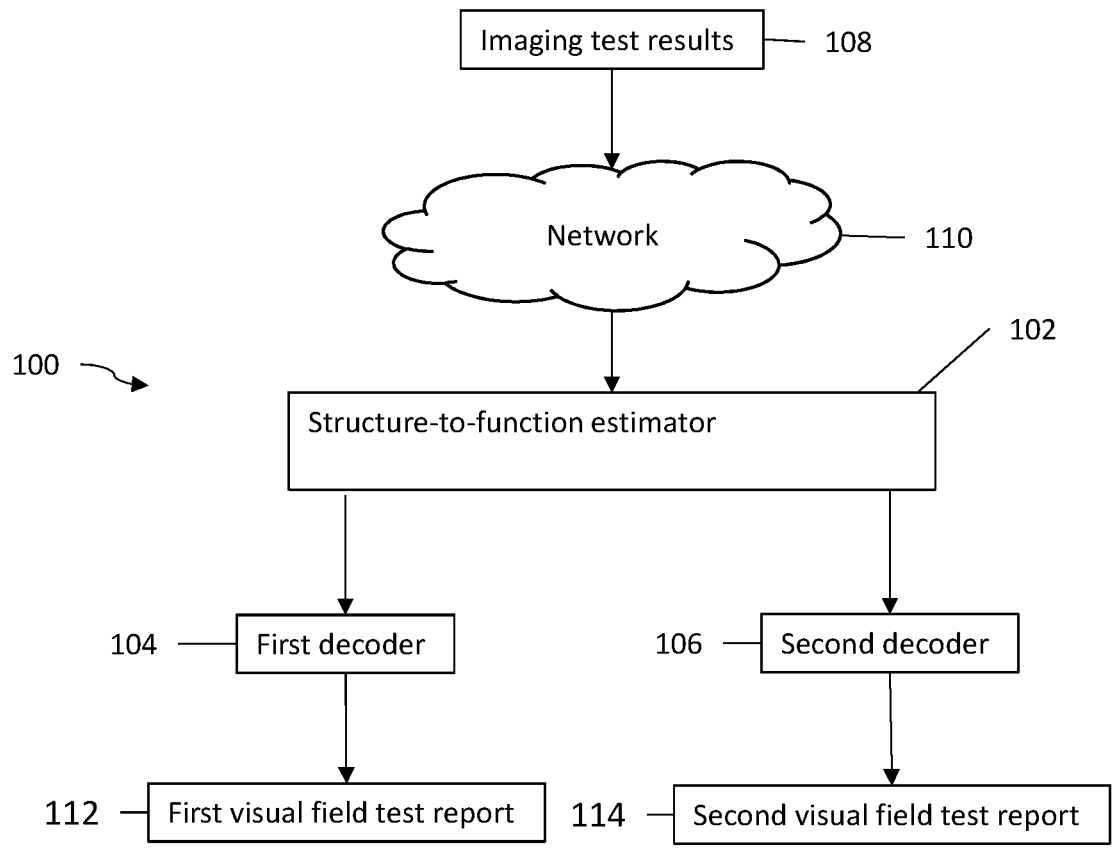
FIG. 1 illustrates a block diagram of components of a system for simulating a visual field test result in accordance with one or more embodiments of the present invention.

The diagrams depicted herein are illustrative. There can be many variations to the diagrams or the operations described therein without departing from the spirit of the invention. For instance, the actions can be performed in a differing order or actions can be added, deleted or modified. Also, the term "coupled" and variations thereof describes having a communications path between two elements and does not imply a direct connection between the elements with no intervening elements/connections between them. All of these variations are considered a part of the specification.

DETAILED DESCRIPTION

One or more embodiments of the present invention provide systems and methods that use a patient's current and prior eye imaging results to simulate visual field test results as if the visual field tests were respectively administered at the time of each imaging test.

During a patient visit for treatment of a progressive eye disease such as glaucoma, a clinician will typically perform eye imaging tests and visual field tests to determine a current state of an eye. An eye imaging test is a non-invasive imaging technique that uses electromagnetic waves to capture two-dimensional and/or three-dimensional images of a patient's eye. Examples of eye imaging include optical coherence tomography (OCT), confocal scanning laser ophthalmoscopy (CSLO), and scanning laser polarimetry (SLP). A visual field test is a method of measuring a patient's central and peripheral visual field function. The visual field test (VFT) can be done using a visual field test instrument that has a display screen. The eye not being tested is covered, and an exact lens correction can be placed in front of the tested eye to improve overall test results. The patient looks into a hemispherical screen, and the VFT instrument displays visual stimuli briefly on the screen in different places in the field of view. The saliency (e.g., contrast or luminance) of the stimuli is manipulated during the test. The patient is instructed to keep looking in the center of the screen and press a button to indicate when the stimuli are detected. The instrument being set to record when the button is pressed, and uses the information to estimate the patient's sensitivity to visual stimulus at different locations of the visual field. The results are typically displayed as visual field maps, which can be used by the clinician to detect loss of sensitivity in the visual field.

There are many types of VFTs, including Amsler grid, static automated perimetry tests, kinetic perimetry tests, and a frequency doubling perimetry tests. In addition to different types of visual field tests, different types of VFT instruments are used to perform different visual field tests. Furthermore, each clinician uses their VFT instrument's settings to their own preference. Additionally, the accuracy visual field test results are heavily dependent on variables that are hard to control. For example, visual field test results depend on the patient's ability to understand the testing instructions, fully cooperate, and complete the entire visual field test in order for the test to generate accurate results. The interpretation of the results can be influenced by many non-ocular factors such as a clinician's tendencies, equipment failure, or misinterpretation of data.

Periodically, patients or clinicians move, patients or clinicians change insurance, or something else occurs to cause a patient to require a new clinician. As a result, patients are not always paired with the same clinician throughout the entire time they are being evaluated for progressive eye disease. Each new clinician who treats the patient may perform the visual field tests differently, such as by using different VFT instruments, or by using the same VFT instrument at different settings. As a result, the visual field test results between the current and previous clinicians are not directly comparable to each other, making tracking eye disease progression across clinics difficult. Additionally, some patients may be unable to perform visual field tests. For example, children and the elderly may not be able to comply with a clinician's instructions or properly interface with the VFT instrument.

One or more embodiments of the present invention address one or more of the above-described shortcomings by providing computer systems, computer-implemented methods, and computer program products configured and arranged to generate simulated visual field test results, based on eye imaging, that overcome the problems associated with the unreliability of visual field tests, and VFT instrument variability. In some embodiments of the invention, a computer system is configured to receive a previously taken image of a patient's eye and generate a simulated result of a selected type of VFT as if it had been performed at the time the image was taken using the selected type of VFT instrument. The selected type of simulated VFT result is generated by processing the image via a structure-to-function estimator that has been trained to perform the task of extracting features that are relevant to visual function in a manner that is not dependent on the specific VFT (or VFT instrument). The extracted features are then processed by a second machine learning model that has been trained to perform the task of simulating a result of the selected type of VFT that would have been achieved using the selected type of VFT instrument.

In an example implementation of embodiments of the invention, patient A has been monitored annually over for progressive eye disease and is now under the care of a new clinician. Patient A's medical file includes three previous annual OCT results, and three previous annual visual field test results, wherein the three previous annual visual field test results were obtained by a type-A VFT instrument. However, when conducting visual field tests on a patient having the general symptoms of patient A, the new clinician has consistently used a type-B VFT instrument. Visual field test results obtained using a type-B VFT instrument are not directly comparable with visual field test results obtained using a type-A VFT instrument. To overcome the visual field test result variation that would result from using different types of VFT instruments, the herein described system is trained to learn structure-to-function relationship in an instrument independent way. Therefore, the system can overcome the visual field test result variations that would result from using two different types of VFT instruments, by simulating the patient's visual field test using the three previous annual OCT results to generate three simulated visual field test results. The generated visual test results are as if they were obtained by a type-B VFT instrument.

In another example implementation of embodiments of the invention, a clinician may have a patient that cannot comply with the requirements of a visual field test. In this instance, the clinician may take an image of the patient's eye and use embodiments of the invention to generate a simulated result of a selected type of visual field test using a selected type of VFT instrument having a selected suite of settings, thereby avoiding the inaccuracies that would be introduced into the visual field test results by the patient's inability to comply with the requirements of the visual field test.

Turning now to FIG. 1, a system 100 for visual field test simulation is generally shown in accordance with one or more embodiments of the present invention. The system 100 includes a structure-to-function estimator 102 that receives an image of an eye as an input and outputs a representation (i.e., a vector) of visual functions in a way that is independent of the VFT instrument configuration used to conduct visual field tests. The structure-to-function estimator 102 is in operable communication with a set of decoders 104 106. Each decoder corresponds to respective VFT instrument configuration. A VFT configuration may be based on a VFT, a VFT device, a VFT device configuration, and/or a VFT performed on a VFT device. A clinician is permitted to select a preferred configuration and the system 100 selects the correct decoder, which translates the representation into a human readable report. It is to be appreciated that although FIG. 1 illustrates a first decoder 104 and a second decoder 106, the system 100 includes a library of decoders, and therefore the system may include any number of decoders greater than one.

In general, the system 100 is operable to receive imaging test results 108 via a communication network 110 and generate a visual field test report 112 114. The imaging test results 106 include two-dimensional and/or three-dimensional image(s) that provide detail about tissue density and location of abnormalities of a patient's eye. The imaging test results 106 are transmitted to the system 100 and the structure-to-function estimator 102 via a communication network 110. The communication network 110 can include the internet, fiber optics, microwave, xDSL (Digital Subscriber Line), Wireless Local Area Network (WLAN) technology, wireless cellular technology, Bluetooth technology and/or any other appropriate communication technology.

The structure-to-function estimator 102 executes a computational model that takes the imaging test results 106 as an input and outputs a representation of a visual function that is independent of any VFT configuration. The representation generated by the structure-to-function estimator 102 is abstract. Therefore, the decoder 104 106 is used to translate the representation into a human readable format displayed on a clinician's computing system.

The structure-to-function estimator 102 receives or has received a preferred configuration of a VFT instrument from a clinician. Based on the preferred configuration, the system 100 selects a decoder 104 106. The decoder 104 106 executes a computational model that translates the representation generated by the structure-to-function estimator 102 and generates a simulated visual field test result report 112 114. The decoder 104 106 is configured to generate a visual field test report 112 114 in a format that is similar to a visual field test report used by the clinician. In some embodiments of the invention, the decoder 104 106 can be in operable communication with a device software, including a third party device software, used by the clinician. Once the decoder 104 106 receives the representation from the structure-to-function estimator 102, it can interface with the device software and provide the simulated visual field test report 112 114 in a substantially similar format as the device software would provide an actual field test result.

The structure-to-function estimator 102 and the decoder 104 106 can include a neural network such as a fully connected deep network (FC), a convolutional neural network (CNN), and a recurrent neural network (RNN). In an exemplary embodiment of the invention, the structure-to-function estimator 102 includes a CNN. The structure-to-function estimator 102 passes the imaging test results 106 through a hierarchical set of learned filters to extract information relevant to visual field function from the image. The structure-to-function estimator 102 takes the extracted features and generates a set of feature maps. The resolution of the feature maps is reduced though a pooling process (e.g., max pooling). The pooling process allows the structure-to-function estimator 102 to focus on the part of the image that provides the most information regarding a particular feature.

The structure-to-function estimator 102 and decoder 104 106 is trained to generate simulated visual field test result reports 112 114. The structure-to-function estimator 102 is paired with different decoders 104 106 to generate respective simulated visual field test result reports 112 114. Each structure-to-function estimator/decoder pair employ respective models that are trained to generate simulated visual field test results based on a VFT instrument configuration.

Training computational models such as the structure-to-function estimator 102 and decoders 104 106 with machine learning algorithms typically require large datasets. Therefore, synthetic data may be generated to increase the size of any training dataset. A dataset may include pasts imaging test results and visual field test results from multiple patients. In some embodiments, the visual field test results are from visual field tests conducted within a threshold time of an imaging test. Therefore, the training imaging test results are paired with visual field test results performed within the threshold time of the respective imaging test results.

The system's ability to generate a representation independent of any VFT configuration, and use that representation to generate a VFT configuration specific VFT report is based on the method of training the system 100. The training data consists of pairs of imaging test results and VFT results, where the VFT results were obtained with different VFT configurations. The training of the system 100 is accomplished by training pairs of the structure-to-function estimator 102 and the appropriate decoder together. Since the structure-to-function estimator 102 is shared among all decoders 104 106, the output of the structure-to-function estimator 102 is forced to become VFT configuration independent, given enough data.

Synthetic data may be created using augmentation techniques that are used to create multiple alterations of the datasets. For example, a received set images may be altered to generating a mirror image, rotating an image, cropping an image, scaling an image, or other alteration. The altered images are, in turn, appended to the original data set to create a larger dataset. The synthetic data may be generated using such as geometric transformations, kernel filters, mixing images, random erasing, feature space augmentation, adversarial training, generative adversarial network (GAN), neural style transfer, and meta-learning.

The structure-to-function estimator/decoder pair models are also trained using ground truth data (i.e., visual field test results). During training, the parameters of the structure-to-function estimator 102 are adjusted based on the ground truth data to minimize the errors between the simulated visual field test results outputted by a decoder 104 106 and actual visual field test results.

The phrases "neural network" and "machine learning" describes a function of electronic systems that learn from data. A machine learning system, engine, or module can include a machine learning algorithm, such as in an external cloud environment (e.g., the cloud computing environment 50 shown in FIG. 4), to learn relationships between inputs and outputs that are currently unknown. In one or more embodiments, machine learning functionality can be implemented using a structure-to-function estimator 102 having the capability to be trained to perform a currently unknown function. In machine learning and cognitive science, neural networks are a family of statistical learning models inspired by the biological neural networks of animals, and in particular, the brain. Neural networks can be used to estimate or approximate systems and functions that depend on a large number of inputs.

The structure-to-function estimator 102 and the first and second decoders 104 106 may be embodied as so-called "neuromorphic" systems of interconnected processor elements that act as simulated "neurons" and exchange "messages" between each other in the form of electronic signals. Similar to the so-called "plasticity" of synaptic neurotransmitter connections that carry messages between biological neurons, the connections in the structure-to-function estimator 102 and the first and second decoders 104 106 carry electronic messages between simulated neurons are provided with numeric weights that correspond to the strength or weakness of a given connection. The weights can be adjusted and tuned based on experience, making the first structure-to-function estimator 102 and the first and second decoders 104 106 adaptive to inputs and capable of learning. After being weighted and transformed by a function determined by the network's designer, the activation of these input neurons are then passed to other downstream neurons, which are often referred to as "hidden" neurons. This process is repeated until an output neuron is activated. Thus, the output neuron is activated and determines (or "learns") which message was read. Multiple pre-neurons and post-neurons can be connected through an array of RSD, which naturally expresses a fully-connected neural network. In the descriptions here, any functionality ascribed to the system 400 can be implemented using the processing system 600 applies.

Figure 2:
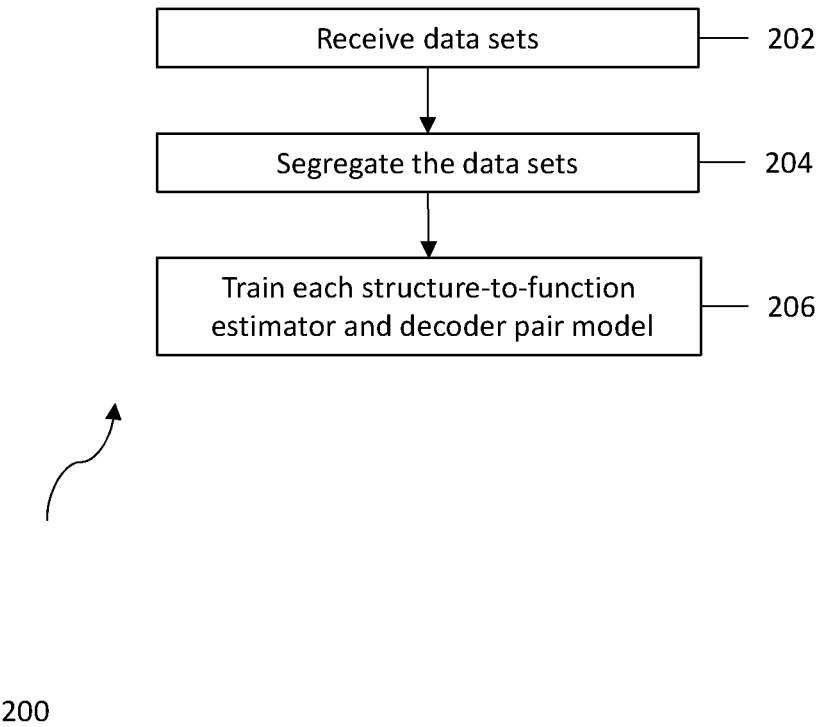
FIG. 2 illustrates a flow diagram of a process for training a system for simulating a visual field test result in accordance with one or more embodiments of the present invention.

Referring to FIG. 2, a flow diagram 200 illustrating a process for training a system for simulating a visual field test result, in accordance with one or more embodiments of the present invention is shown. At block 202, the system receives a training set of datasets, including combinations of imaging test results and visual field test results for training different models. The datasets include imaging test results and visual field test results that were obtained using different VFT instrument configurations. VFT instrument configurations may differ based on a VFT, a VFT instrument, and a VFT instrument setting configuration. At block 204, the data sets are segregated based on a VFT instrument configuration. At block 206, for each VFT instrument configuration, the structure-to-function estimator and the respective decoder is trained based on a respective VFT instrument configuration.

Figure 3:
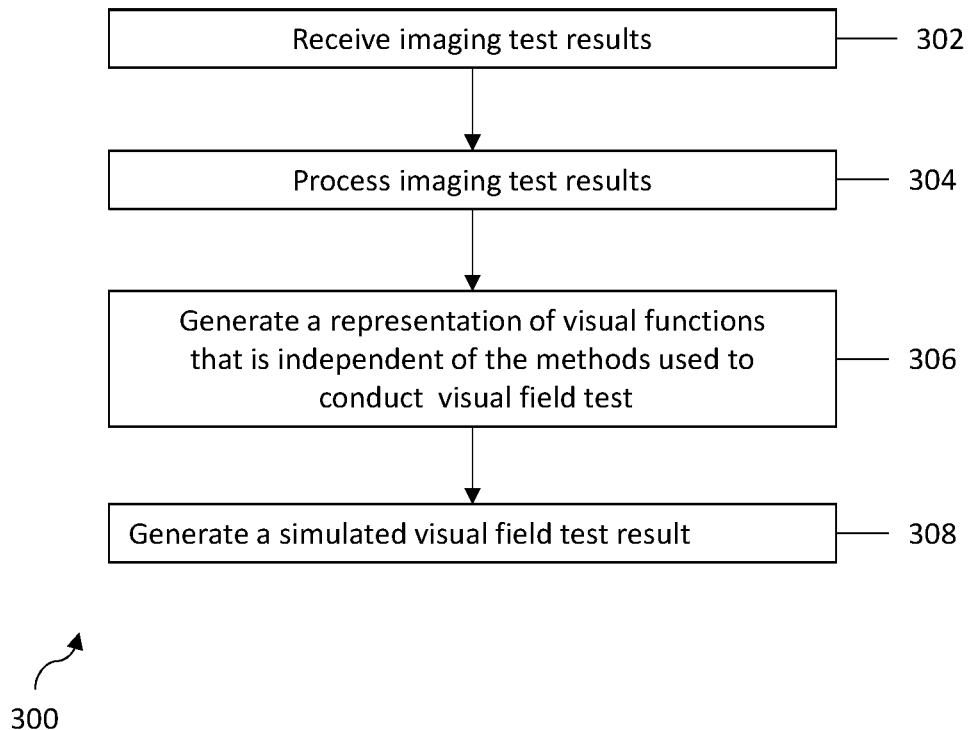
FIG. 3 illustrates a flow diagram of a process for simulating a visual field test result in accordance with one or more embodiments of the present invention.

Referring to FIG. 3, a flow diagram 300 illustrating a process for simulating a visual field test result in accordance with one or more embodiments of the present invention is shown. At block 302, a system receives at least one image of a patient's eye obtained from an imaging test. The image may have been obtained from a previous clinician of the patient or it may have been previously obtained by the patient's current clinician. At block 304, the system processes the eye image(s) to extract features related to the patent's visual functioning. At block 306, the system generates a representation of the patient visual functioning. The representation is independent of any VFT instrument configuration. At block 308, the clinician selects a preferred VFT configuration system generates simulated visual field test results for displaying on a clinician's computing system.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 4:
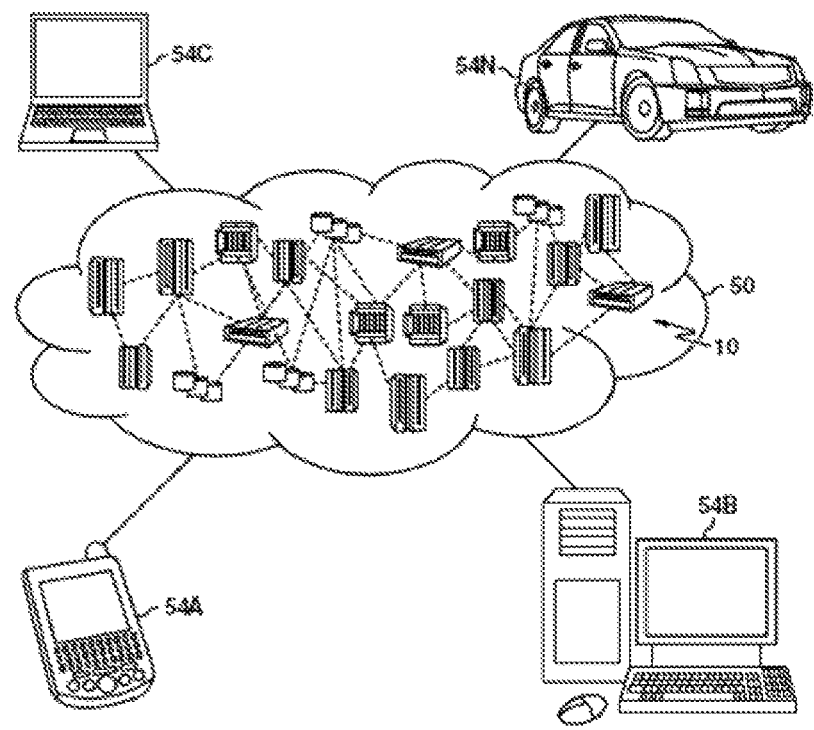
FIG. 4 depicts a cloud computing environment according to one or more embodiments of the present invention.

Referring now to FIG. 4, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 4 are intended to be illustrative only and that computing nodes 10 and cloud computing environment 50 can communicate with any type of computerized device over any type of network and/or network addressable connection (e.g., using a web browser).

Figure 5:
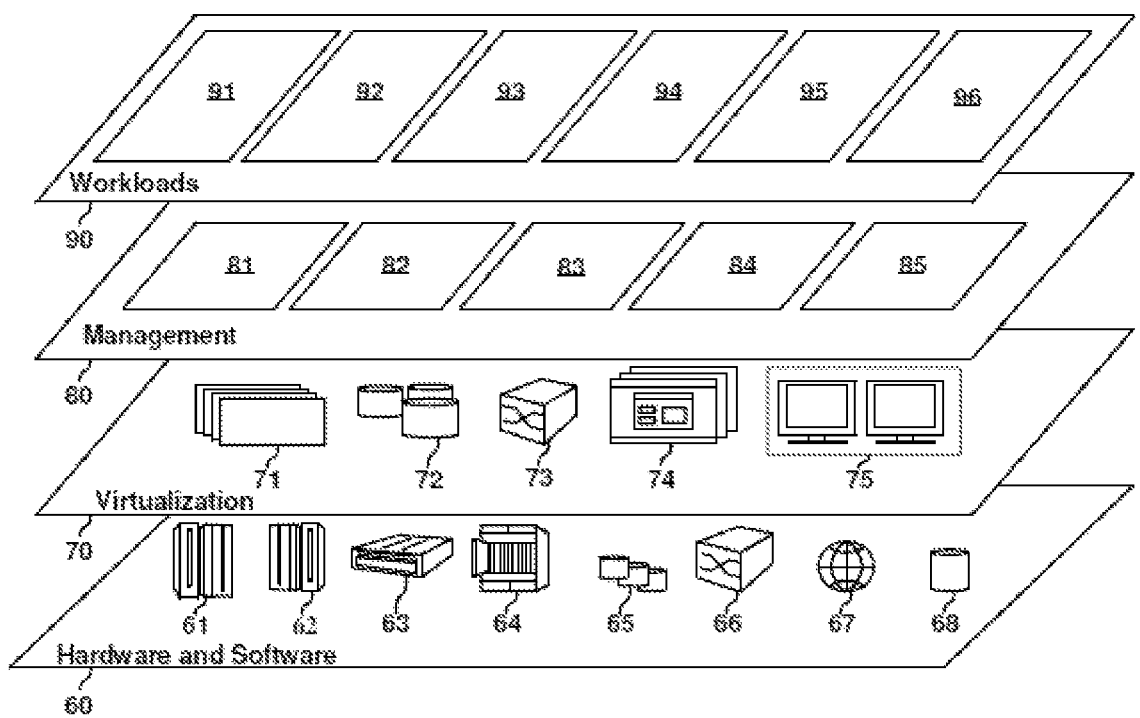
FIG. 5 depicts abstraction model layers according to one or more embodiments of the present invention.

Referring now to FIG. 5, a set of functional abstraction layers provided by cloud computing environment 50 (FIG. 4) is shown. It should be understood in advance that the components, layers, and functions shown in FIG. 5 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and generating a simulated visual field test 96.

Figure 6:
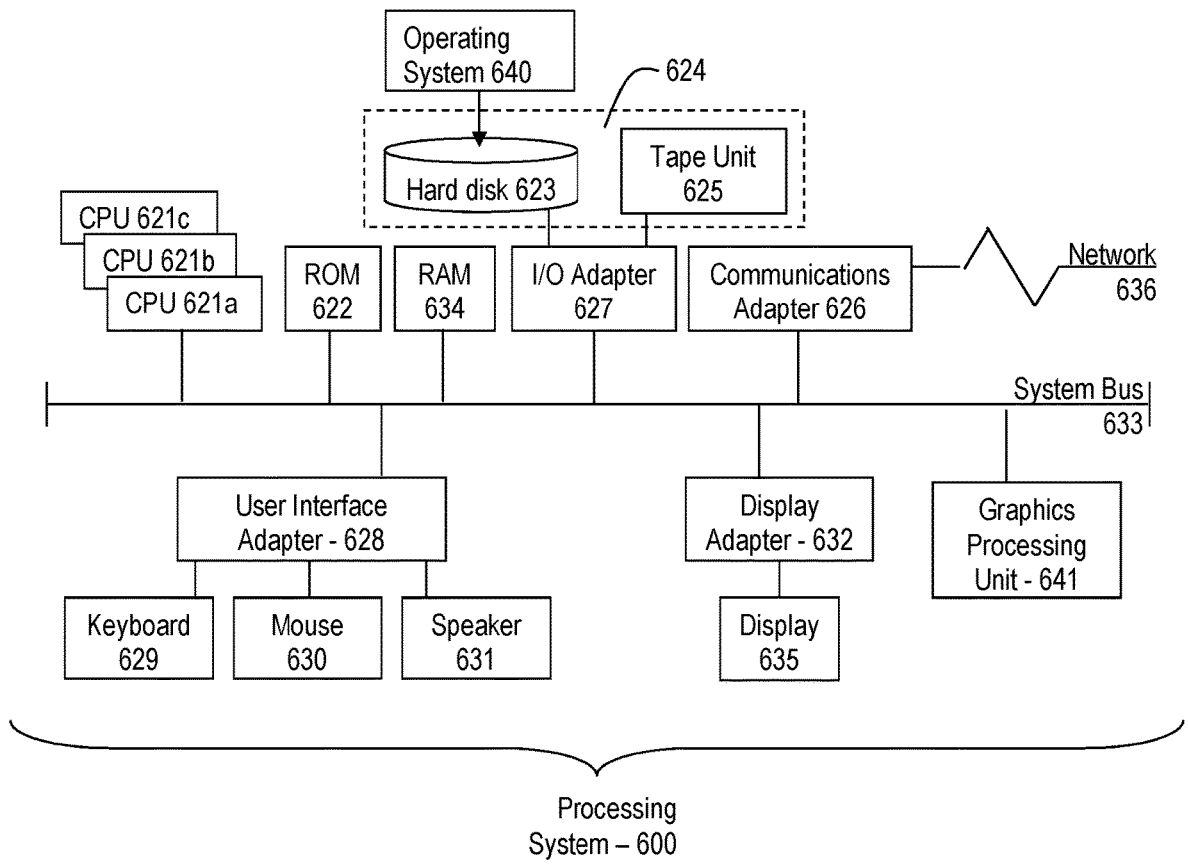
FIG. 6 depicts a block diagram of a computer system for use in implementing one or more embodiments of the present invention.

It is understood that the present disclosure is capable of being implemented in conjunction with any other type of computing environment now known or later developed. For example, FIG. 6 depicts a block diagram of a processing system 600 for implementing the techniques described herein. In examples, the processing system 600 has one or more central processing units (processors) 621a, 621b, 621c, etc. (collectively or generically referred to as processor(s) 621 and/or as processing device(s)). In aspects of the present disclosure, each processor 621 can include a reduced instruction set computer (RISC) microprocessor. Processors 621 are coupled to system memory (e.g., random access memory (RAM) 624) and various other components via a system bus 633. Read only memory (ROM) 622 is coupled to system bus 633 and may include a basic input/output system (BIOS), which controls certain basic functions of the processing system 600.

Further depicted are an input/output (I/O) adapter 627 and a network adapter 626 coupled to the system bus 633. I/O adapter 627 may be a small computer system interface (SCSI) adapter that communicates with a hard disk 623 and/or a storage device 625 or any other similar component. I/O adapter 627, hard disk 623, and storage device 625 are collectively referred to herein as mass storage 764. Operating system 640 for execution on processing system 600 may be stored in mass storage 634. The network adapter 626 interconnects system bus 633 with an outside network 636 enabling processing system 600 to communicate with other such systems.

A display (e.g., a display monitor) 635 is connected to the system bus 633 by display adapter 632, which may include a graphics adapter to improve the performance of graphics intensive applications and a video controller. In one aspect of the present disclosure, adapters 626, 627, and/or 632 may be connected to one or more I/O buses that are connected to the system bus 633 via an intermediate bus bridge (not shown). Suitable I/O buses for connecting peripheral devices such as hard disk controllers, network adapters, and graphics adapters typically include common protocols, such as the Peripheral Component Interconnect (PCI). Additional input/output devices are shown as connected to system bus 633 via user interface adapter 628 and display adapter 632. An input device 629 (e.g., a keyboard, a microphone, a touchscreen, etc.), an input pointer 630 (e.g., a mouse, trackpad, touchscreen, etc.), and/or a speaker 631 may be interconnected to system bus 633 via user interface adapter 628, which may include, for example, a Super I/O chip integrating multiple device adapters into a single integrated circuit In some aspects of the present disclosure, the processing system 600 includes a graphics processing unit 637. Graphics processing unit 637 is a specialized electronic circuit designed to manipulate and alter memory to accelerate the creation of images in a frame buffer intended for output to a display. In general, graphics processing unit 637 is very efficient at manipulating computer graphics and image processing and has a highly parallel structure that makes it more effective than general-purpose CPUs for algorithms where processing of large blocks of data is done in parallel.

Thus, as configured herein, the processing system 600 includes processing capability in the form of processors 621, storage capability including system memory (e.g., RAM 724), and mass storage 634, input means such as keyboard 629 and mouse 630, and output capability including speaker 631 and display 635. In some aspects of the present disclosure, a portion of system memory (e.g., RAM 724) and mass storage 634 collectively store the operating system 640 to coordinate the functions of the various components shown in the processing system 600.

Various embodiments of the invention are described herein with reference to the related drawings. Alternative embodiments of the invention can be devised without departing from the scope of this invention. Various connections and positional relationships (e.g., over, below, adjacent, etc.) are set forth between elements in the following description and in the drawings. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. Moreover, the various tasks and process steps described herein can be incorporated into a more comprehensive procedure or process having additional steps or functionality not described in detail herein.

One or more of the methods described herein can be implemented with any or a combination of the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

For the sake of brevity, conventional techniques related to making and using aspects of the invention may or may not be described in detail herein. In particular, various aspects of computing systems and specific computer programs to implement the various technical features described herein are well known. Accordingly, in the interest of brevity, many conventional implementation details are only mentioned briefly herein or are omitted entirely without providing the well-known system and/or process details.

In some embodiments, various functions or acts can take place at a given location and/or in connection with the operation of one or more apparatuses or systems. In some embodiments, a portion of a given function or act can be performed at a first device or location, and the remainder of the function or act can be performed at one or more additional devices or locations.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The present disclosure has been presented for purposes of illustration and description, but is not intended to be exhaustive or limited to the form disclosed. Many modifications and variations will be apparent to those of ordinary skill in the art without departing from the scope and spirit of the disclosure. The embodiments were chosen and described in order to best explain the principles of the disclosure and the practical application, and to enable others of ordinary skill in the art to understand the disclosure for various embodiments with various modifications as are suited to the particular use contemplated.

The diagrams depicted herein are illustrative. There can be many variations to the diagram or the steps (or operations) described therein without departing from the spirit of the disclosure. For instance, the actions can be performed in a differing order or actions can be added, deleted or modified. Also, the term "coupled" describes having a signal path between two elements and does not imply a direct connection between the elements with no intervening elements/connections therebetween. All of these variations are considered a part of the present disclosure.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" are understood to include any integer number greater than or equal to one, i.e. one, two, three, four, etc. The terms "a plurality" are understood to include any integer number greater than or equal to two, i.e. two, three, four, five, etc. The term "connection" can include both an indirect "connection" and a direct "connection."

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instruction by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A computer-implemented method comprising:
    processing, by a processor, eye image data to extract visual functioning related features;
    generating, by the processor, a representation of a visual function of the eye that is independent of a visual field test (VFT) configuration; and
    generating, by the processor, a simulated VFT configuration specific test result based at least in part on the representation.

2. The computer-implemented method of claim 1, wherein the VFT configuration comprises a VFT device type or a VFT device setting.

3. The computer-implemented method of claim 1, wherein the VFT configuration comprises a VFT.

4. The computer-implemented method of claim 1, further comprising:
    interfacing with a visual field testing software on a computing system; and
    providing the simulated device specific test result in a format similar to a format generated by the visual field testing software.

5. The computer-implemented method of claim 1, wherein the eye image data was obtained using optical coherence tomography.

6. The computer-implemented method of claim 1, wherein the VFT configuration specific test result is generated by a decoder of a plurality of decoders.

7. The computer-implemented method of claim 6 further comprising:
    receiving a selection of a VFT configuration; and
    selecting the decoder of the plurality of decoders based on the selection.

8. A system comprising:
    a memory having computer readable instructions; and
    one or more processors for executing the computer readable instructions, the computer readable instructions controlling the one or more processors to perform operations comprising:
        processing eye image data to extract visual functioning related features;
        generating a representation of a visual function of the eye that is independent of a visual field test (VFT) configuration; and
        generating a simulated VFT configuration specific test result based at least in part on the representation.

9. The system of claim 8, wherein the VFT configuration comprises a VFT device type or a VFT device setting.

10. The system of claim 8, wherein the VFT configuration comprises a VFT.

11. The system of claim 8, the operations further comprising:
  interfacing with a visual field testing software on a computing system; and
  providing the simulated device specific test result in a format similar to a format generated by the visual field testing software.

12. The system of claim 8, wherein the eye image data was obtained using optical coherence tomography.

13. The system of claim 8, wherein the VFT configuration specific test result is generated by a decoder of a plurality of decoders.

14. The computer-implemented method of claim 13, the operations further comprising:
  receiving a selection of a VFT configuration; and
  selecting the decoder of the plurality of decoders based on the selection.

15. A computer program product comprising a computer readable storage medium having program instructions embodied therewith, the program instructions executable by a processor to cause the processor to perform operations comprising:
  processing eye image data to extract visual functioning related features;
  generating a representation of a visual function of the eye that is independent of a visual field test (VFT) configuration; and
  generating a simulated VFT configuration specific test result based at least in part on the representation.

16. The computer program product of claim 15, wherein the VFT configuration comprises a VFT device type or a VFT device setting.

17. The computer program product of claim 15, wherein the VFT configuration comprises a VFT.

18. The computer program product of claim 15, the operations further comprising:
  interfacing with a visual field testing software on a computing system; and
  providing the simulated device specific test result in a format similar to a format generated by the visual field testing software.

19. The computer program product of claim 15, wherein the eye image data was obtained using optical coherence tomography.

20. The computer program product of claim 15, wherein the VFT configuration specific test result is generated by a decoder of a plurality of decoders.

* * * * *